Figure 1:
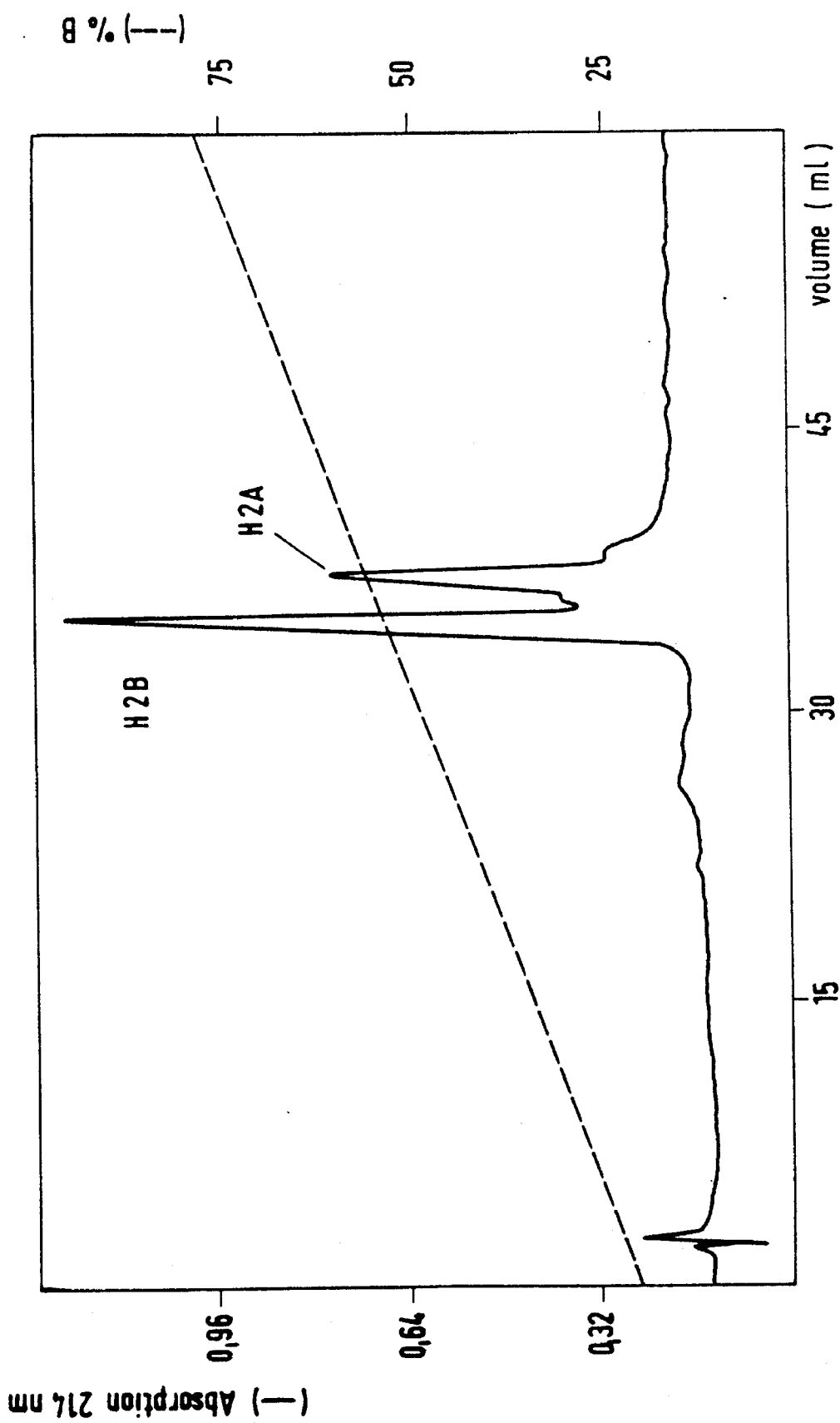

United States Patent [19]
Zeppezauer et al.

[11] Patent Number: 5,578,571
[45] Date of Patent: Nov. 26, 1996

[54] CYTOSTATIC OR CYTOTOXIC COMBINATION OF ACTIVE SUBSTANCES FOR USE IN THERAPEUTIC PROCEDURES

[75] Inventors: Michael Zeppezauer, Scheidt; Hans P. Leinenbach, Riegsberg, both of Germany

[73] Assignee: Symbiotec Gesellschaft zur Forschung und Entwicklung auf dem Gebiet der Biotechnologie mbH, Herborn, Germany

[21] Appl. No.: 310,378

[22] Filed: Sep. 22, 1994

Related U.S. Application Data

[63] Continuation of Ser. No. 635,709, Dec. 28, 1990, abandoned.

[30] Foreign Application Priority Data

Jan. 4, 1990 [DE] Germany .......................... 40 00 154.7

[51] Int. Cl.⁶ .......................... A61K 38/00; A01N 37/18; C07K 5/00; C07K 7/00
[52] U.S. Cl. .................. 514/12; 514/2; 530/324
[58] Field of Search .......................... 514/2, 12; 530/324

[56] References Cited

U.S. PATENT DOCUMENTS 4,902,505  2/1990  Pardridge et al. .................... 424/85.7

OTHER PUBLICATIONS

Buxman, J. Invest. Derm., vol. 73, No. 3, pp. 250–255, 1979.
Ginsburg et al., Biological Abstracts, vol. 78, 8, 1984, Abst No. :59767.

*Primary Examiner*—Avis M. Davenport
*Attorney, Agent, or Firm*—Kanesaka & Takeuchi

[57] ABSTRACT

According to this invention the combination of active substances for use in therapeutic procedures consists of at least one cytostatic compound, e.g. vincristine, methotrexate, cisplatin as the first agent and at least one histone and/or one active histone fragment with cytostatic or cytotoxic activity as the second agent. Both active agents act synergistically at the site of the pathogenic process.

5 Claims, 4 Drawing Sheets

CYTOSTATIC OR CYTOTOXIC COMBINATION OF ACTIVE SUBSTANCES FOR USE IN THERAPEUTIC PROCEDURES

This application is a continuation of U.S. application Ser. No. 07/635,709 filed Dec. 28, 1990 and now abandoned, which is incorporated herein by reference.

Cytostatic drugs have widespread medical use e.g. in the therapy of malignant diseases. The successful therapy of neoplastic diseases depends critically on the early diagnosis and removal of the tumors. Radiation therapy is applied successfully for locally restricted tumors and is also combined successfully with surgical therapy. In the case of disseminating tumors and metastases treatment is restricted to chemotherapy and immunotherapy. Chemotherapeutic treatments are usually accompanied by severe side effects such as damage of Kidneys and liver, disturbances of the hematopoietic system and other kinds of damage impairing the patient's general well-being and resistance. In addition, most cytostatic agents act as strong immunosuppressive agents. These side effects often necessitate a dosage of cytostatics which is not sufficiently high for the therapeutic purpose, or they demand an interruption of the treatment.

Often the prolonged use of cytostatic drugs leads to the selection of resistant cancer cells which ultimately cause the death of the patient. Finally, these are cancer cells which are totally insensitive against the known cytostatic agents.

Immunotherapy based on interferons and interleukins is applied mainly in order to stimulate the cellular resistance. In general immunotherapy consists of supportive, additive measures without independent therapeutic potential in the malignant process.

The immunosuppressive effect of cytostatic substances has rendered them useful in,the therapy of autoimmune diseases such as multiple sclerosis, psoriasis and certain rheumatic diseases. Even here their beneficial effect has to be weighed against the serious side effects which necessitate too low dosages and/or interruption of the treatment.

It is the object of the present invention to provide a combination of active substances which results in a significantly improved cytostatic or cytotoxic effect as compared to conventional cytostatics given alone, e.g. vincristin, methotrexate, cisplatin etc. Thereby, chemotherapies may be offered which combine increasing efficiency with a large reduction of side effects and therapeutic doses. Thus, the therapeutic efficiency of known cytostatic drugs is increased. Also, certain cell lines which are insensitive to chemotherapeutic treatment may become susceptible to chemotherapy by applying the combination of active substances.

The European patent application 85 100 179.2 has already revealed that at least one histone and/or one histone fragment may show hormonal effect which may be used favourably in the treatment of cancer. This applies in particular to the histones H1, H2A and/or H2B and H3.

In the German published patent application 37 37 274 the direct cytotoxic action on certain cancer cell lines of the mixture of histones H2A/H2B has been demonstrated. The cytotoxic action on certain malignant cell lines of histone H1 has been demonstrated in the U.S. patent application Ser. No. 07/332 658 of 3rd April 1989. Said application is a CIP of the U.S. patent application Ser. No. 777,783 of 10th January 1985, published as U.S. Pat. 4,818,763.

The object is solved by the invention specified in the claims section.

The efficiency of the combination of active substances according to the invention is demonstrated by the results of the following experiments visualized by the enclosed FIGS. 1–7.

In each case a mixture or complex of histones H2A and H2B was used according to FIG. 1. It had been obtained by High Performance Lignid Chromatography (HPLC) from a preparation of the Homeostatic Thymus Hormone from calf thymus (Bernardi G. & Comsa J., Purification chromatographigne d'une preparation de thymus doneé d'activité hormonale, Experienta 21, 416–417, 1965).

Elution was performed from a μBondapak C18 column using a linear gradient (% B) from 20 to 80% acetonitrile in 0,1% trifluoro acetic acid. The flow rate was 1 ml/min. The eluate was monitored by measuring the optical absorption at 214 nm. In FIG. 1 on the abscissa the effluent volume is depicted, on the left ordinate the absorption at 214 nm and on the right ordinate the linear gradient (% B).

Accordingly the pure histones H2A and H2B can be prepared. It remains to be shown whether H2A:H2B (FIG. 1) is a mixture of H2A and H2B or a chemical complex of both molecules. It is obvious that other known procedures for the preparation of pure histones may be used. Thus the invention is not restricted to the utilization of H2A:H2B; rather, it includes their active parts or fragments with cytostatic and cytotoxic effect. Although the mechanismn of the cytotoxic or cytostatic action of histones or of their active parts or fragments is not yet understood the inventors have reasons to believe that the repetitive amino acid sequences KRAA and KRVA and their environments play an active part in the biological action of said molecules. The sequence KRAA is found in the C-terminal part of histone H1 and the sequence KRVA is found in the N-terminal part of histone H2B.

The malignant cells were grown in culture medium completed with fetal calf serum (FCS). The culture medium RPMI 1640 with 10% FCS was renewed daily. When the bottom of the culture flask was covered completely with cells these were scratched off gently and partly transferred to another flask in order to obtain cells under optimal growth conditions. Incubation was performed at 36,5° C. and 5,5% carbon dioxide in a controlled incubator.

The concentration of living cells was determined using the dye Nigrosin (0,2% in phosphate-buffered saline i.e. PBS) in the Neubauer chamber.

The components of the combined chemotherapeutic agent according to this invention (e.g. H2A:H2B and a known cytostatic agent) were added to the culture medium either alone or combined according to the invention and the solutions were subjected to sterile filtration.

For the purpose of the experiments the malignant cells were scratched off the bottom of those culture flasks which were not covered too tightly by cells. The number of living cells was determined and adjusted to $3,5 \times 10^5$ cells/ml. Part of this cell suspension was mixed with the combined chemotherapeutic agent or its single components and placed in the incubator. The final concentration of malignant cells was $1,75 \times 10^5$ cells/ml in each well.

EXPERIMENT 1

Figure 2:
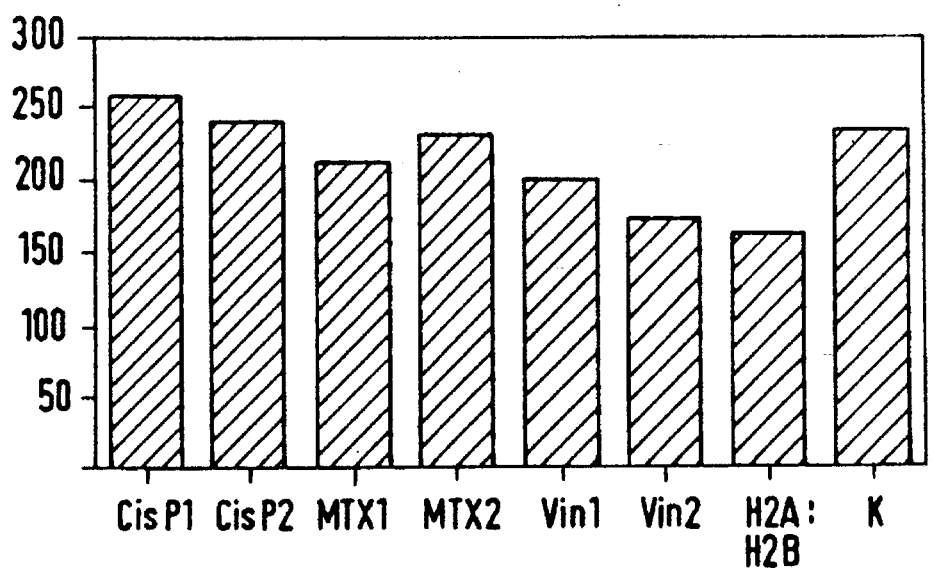

The lymphoma cell line OH77 was used to test the efficiency of the combination of H2A:H2B with either cisplatin or methotrexate, or vincristine. FIG. 2 shows the results of this cytotoxicity test with said cytostatic agents and H2B:H2A alone. Cells of the cell line OH77 were incubated for 48 hours with 1 μg/ml Cisplatin (CisP1), or 2 μg/ml Cisplatin (CisP2), or 5 μg/ml methotrexate (MTX1), or 10 μg/ml methotrexate (MTX2), or 5 μg/ml vincristine (Vin1), or 10 μg/ml vincristine (Vin2), or 250 μg/ml H2A:H2B and the growth rate was determined in percent. K indicates the control experiment where the growth rate was determined without addition of a cytostatic agent or H2A:H2B for 48 hours. The cytostatic agents alone or H2A:H2B alone showed small or no cytostatic effects at all.

Figure 3:
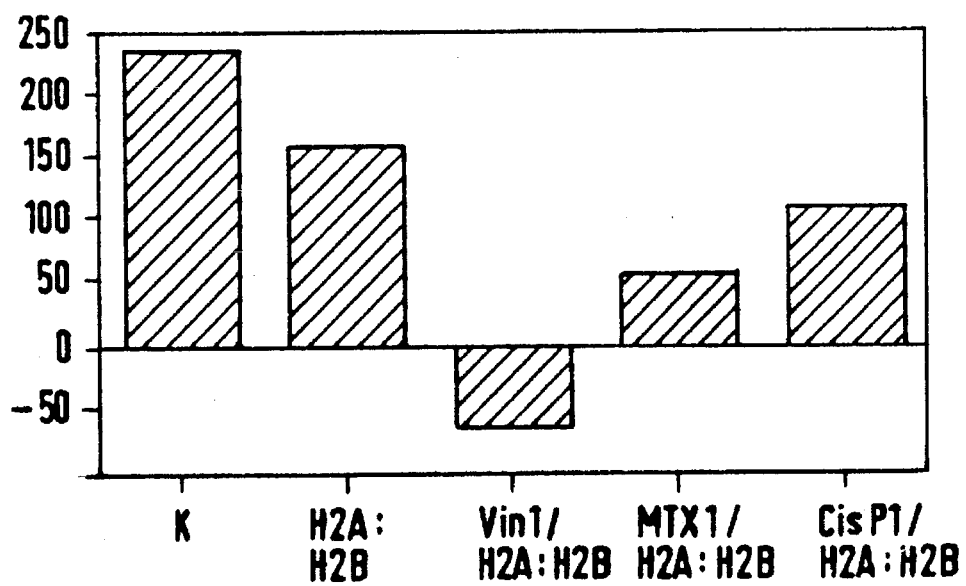

FIG. 3 shows another cytotoxicity test in which each of the above-mentioned cytostatics was used in combination with H2A:H2B. Cells of the OH77 cell line were incubated for 48 h with 100 µg/ml H2A:H2B and 5 µg/ml vincristine (Vin1/H2A:H2B), or 5 µg/ml methotrexate (MTX1/H2A:H2B), or 1 µg/ml Cisplatin (CisP1/H2A:H2B) and the growth rate was determined. K depicts again the growth rate for 48 hours in the absence of any agent. For better comparison the cytostatic effect of 100 µg/ml H2B:H2A alon is also shown.

A clear synergistic action resulting in a cytotoxic effect is demonstrated by combining vincristine and H2A:H2B in concentrations each of which alone shows only a slight cytostatic effect (FIG. 2).

An improvement of the cytostatic action by the combination of H2A:H2B with methotrexate or with cisplatin is seen compared to the action of the components alone. This is particularly clear in the case of methotrexate.

EXPERIMENT 2

Figure 4:
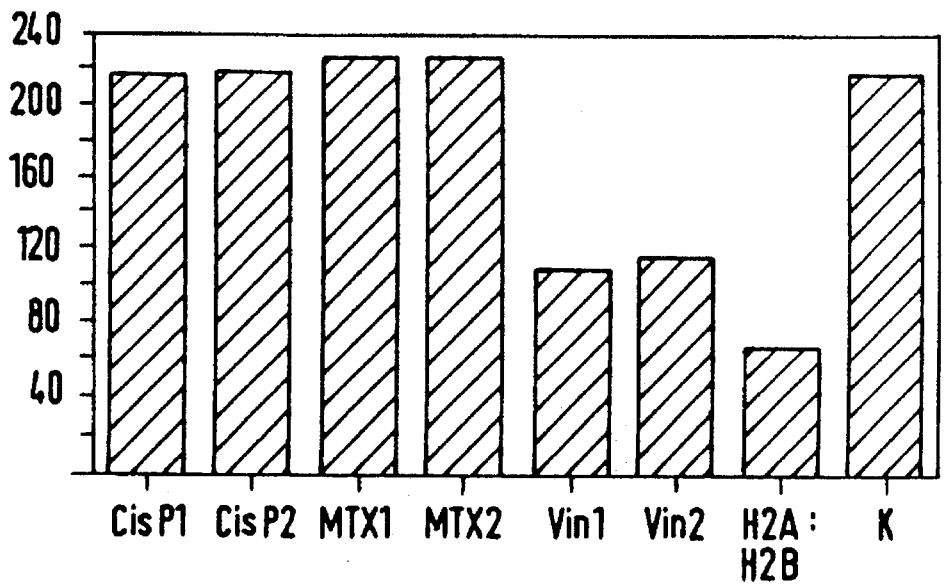

The efficiency of H2A:H2B combined with the above-mentioned cytostatic drugs was also tested in vitro with the melanoma cell line EG 463. FIG. 4 Shows the results of a cytotoxicity test with said cytostatics and H2A:H2B alone. Cells of the melanoma cell line EG 463 were incubated for 48 hours with the following substances alone and the growth rate was noted in %.

CisP1 (1 µg/ml Cisplatin), CisP2 (2 µg/ml Cisplatin), MTX1 (5 µg/ml methotrexate), MTX2 (10 µg/ml methotrexate), Vin1(5 µg/ml vincristine), Vin2 (10 µg/ml vincristine), and 250 µg/ml H2A:H2B. K depicts again the control experiment devoid of any agent.

Figure 5:
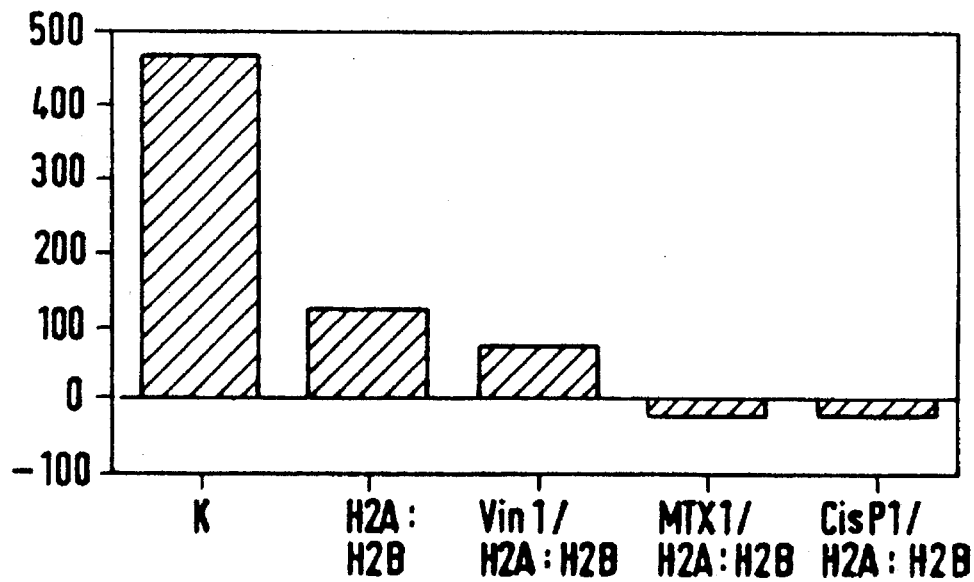

In FIG. 5 the cells of the melanoma cell line EG 463 were incubated for 48 hours with the above-mentioned cytostatic agents in combination with H2A:H2B and the growth rate was determined:
Vin1/H2A:H2B (5 µg/ml vincristine+100 µg/ml H2A:H2B),
MTX1/H2A:H2B (5 µg/ml methotrexate+100 µg/ml H2A:H2B),
CisP1/H2A:H2B (1 µg/ml cisplatin+100 µg/ml H2A:H2B), K depicts again the control experiment devoid of any addition and H2A:H2B shows the cytostatic action of 100 µg/ml H2A:H2B alone. It is evident from FIG. 5 that the combination of H2A:H2B and vincristine which alone exert a slightly cytostatic action (FIG. 4) is characterized not by a snyergistic effect but rather a mere additive one.

In contrast, methotrexate and cisplatin which given alone are inefficient (FIG. 4) show a cytotoxic effect when each of them is administered in combination with H2A:H2B. this again demonstrates the snyergism resulting from the combination of H2A:H2B with methotrexate and cisplatin, respectively.

EXPERIMENT 3

Figure 6:
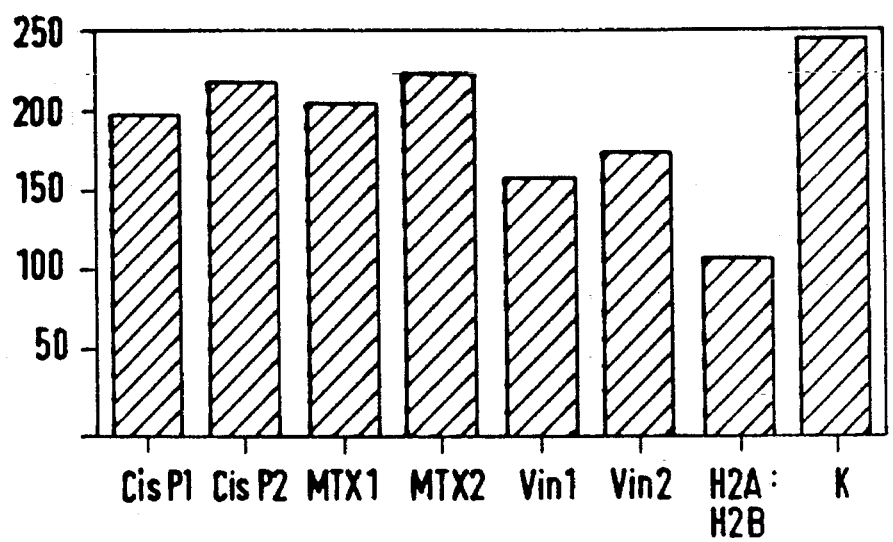

The efficiency against nontransformed human fibroblasts was tested in vitro using the combination of H2A:H2B with the above-mentioned cytostatic drugs. FIG. 6 shows the data obtained with either the cytostatic agents or the H2A:H2B alone which were tested against the Hufibl fibroblast cell line. Cells of this cell line were incubated for 48 hours with one of the following substances and the growth rate was monitored and expressed in %.

CisP1 (1 µg/ml cisplatin), CisP2 (2 µg/ml cisplating), MTX1 (5 µg/ml methotrexate), MTX2 (10 µg/ml methotrexate), Vin1(5 µg/ml vincristine), Vin2 (10 µg/ml vincristine), and 250 µg/ml H2A:H2B. K depicts again the control experiment without any additive for 48 hours.

Figure 7:
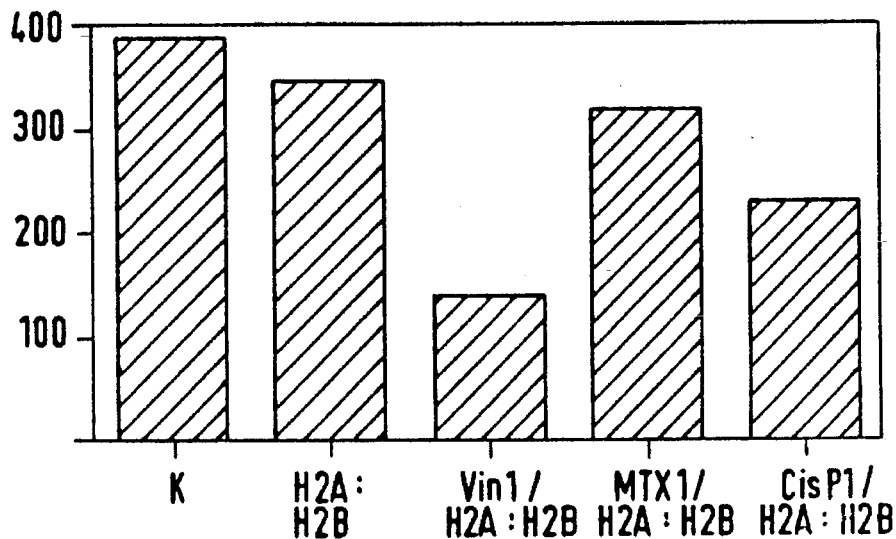

In FIG. 7 the data are obtained by incubating for 48 hours cells of the human fibroblast line Hufibl with one of the above-mentioned cytostatic agents combined with H2A:H2B and monitoring the growth rate as follows:
Vin1/H2A:H2B (5 µg/ml vincristin+100 µg/ml H2A:H2B),
MTX1/H2A:H2B (5 µg/ml methotrexate+100 µg/ml H2A:H2B), and
CisP1/H2A:H2B (1 µg/ml cisplatin+100 µg/ml H2A:H2B).

In addition the above-mentioned cell line was incubated solely with 100 µg/ml H2A:H2B for comparison. K depicts again the control experiment devoid of any addition.

The data show that no synergistic effect is observed upon the combined action of H2A:H2B and cytostatic agents against non-transformed human fibroblasts. The measurable, cytostatic action of the cytostatic compounds is enhanced by H2A:H2B (FIG. 7) but it is not changed into a cytotoxic one.

This invention is not restricted to the combination of H2A:H2B, be it a mixture or a complex, with cytostatic compounds. It is to be expected that similar effects are observed upon combining the single histones H2A or H2B with cytostatic drugs. It is also expected that comparable effects will be achieved by combining histones H1 and H3 with cytostatic drugs. Furthermore, it is obvious for the expert that entire histone molecules may be replaced by their active parts which are composed of at least four or five amino acid residues exhibiting cytostatic or cytotoxic properties.

Finally, this invention is not limited with respect to the above-mentioned cytostatic compounds. Accordingly, the expert has the choice to combine any other suitable cytostatic compound with at least one histone or histone fragment in order to create novel chemotherapeutic drugs possessing increased therapeutic efficiency and enabling lower dosage. The advantages of these combined drugs are:
(i) an increased cytostatic efficiency gained simultaneously with reduced side effects,
(ii) the possibility of creating novel, combined chemotherapeutic drugs which exert a cytotoxic action on tumor cells in contrast to a cytostatic effect of the single components of the drug,
(iii) the possibility of achieving a positive therapeutic response with cytostatic drugs which alone are inefficient against certain tumor cell lines or certain autoimmune diseases.

Administration of histones (to experimental animals, e.g. mice, rats, guinea pigs, sheep) does not cause any detectable side effects. Therefore, in accordance with this invention it is now possible to perform chemotherapy with a higher chance of success over a longer time period. Simultaneously the extent of side effects may be decreased to an acceptable level.

As to the mode of administration, it should be emphasized that it is the combination of therapeutic agents which gives rise to its synergistic therapeutic effect at the site of the pathogenic process no matter whether the first and the second agent are administered together or separately. Therefore, the two agents may be given together in a single dose or in separate ones with respect to space and time.

Depending on the choice of the first and the second agent and their respective, pharmacokinetic behaviour the two substances may be administered also at different times if this achieves that they reach their optimal concentration at the site of the pathogenic process at a certain time.

Although the experiments described above demonstrate the efficiency of the combination of therapeutic agents according to the invention only with respect to malignant lymphoma and melanoma, the invention is not restricted to the therapy of malignancies.

It is obvious to use combinations of therapeutic agents according to this invention also for the treatment of autoimmune diseases.

We claim:

1. A composition having cytostatic or cytotoxic effects on lymphoma cells, comprising:

a therapeutically acceptable carrier and, in quantities having in combination of two active substances a synergistic therapeutic effect at the lymphoma cells, vincristin as one of said two active substances and at least one histone selected from the group consisting of H1, H2A, H2B, and a dimer H2A:H2B.

2. The composition of claim 1, wherein said histones and vincristine are 100 µg/ml of H2A:H2B and 5 µg/ml of vincristine, respectively.

3. A composition having cytostatic or cytotoxic effects on melanoma cells, comprising:

a therapeutically acceptable carrier and, in quantities having in combination of two active substances a synergistic therapeutic effect at the melanoma cells, a cytostatic agent selected from the group consisting of methotrexate and cisplantin as one of said two active substances and at least one histone selected from the group consisting of H1, H2A, H2B, and dimer H2A:H2B.

4. The composition of claim 3, wherein said histones and cytostatic agent are 100 µg/ml of H2A:H2B and 5 µg/ml of methotrexate, respectively.

5. The composition of claim 3, wherein said histones and cytostatic agent are 100 µg/ml of H2A:H2B and one µg/ml of cisplatin.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Bos taurus
        ( D ) DEVELOPMENTAL STAGE: Calf
        ( F ) TISSUE TYPE: Thymus ( x i ) SEQUENCE DESCRIPTION: SEQ ID NO:1:

Lys  Arg  Val  Ala
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Bos taurus
        ( D ) DEVELOPMENTAL STAGE: Calf
        ( F ) TISSUE TYPE: Thymus ( x i ) SEQUENCE DESCRIPTION: SEQ ID NO:2:

Lys  Arg  Ala  Ala
    1